United States Patent [19]

Nagase et al.

[11] Patent Number: 5,046,507
[45] Date of Patent: Sep. 10, 1991

[54] TEAR PRODUCTION MEASURING SHEET AND PACKAGE THEREFOR

[75] Inventors: Makoto Nagase, Kawasaki; Kuniaki Asami, Tokyo; Shuichi Kobayashi, Tokyo; Yasunori Arai, Tokyo; Kazuo Ito, Tokyo; Motohiro Oka, Tokyo, all of Japan

[73] Assignee: Showa Yakuhin Kako Co., Ltd., Japan

[21] Appl. No.: 495,324

[22] Filed: Mar. 19, 1990

[30] Foreign Application Priority Data

Mar. 20, 1989 [JP] Japan ................................. 1-31567

[51] Int. Cl.$^5$ ............................................. A61B 5/00
[52] U.S. Cl. .................................... 128/745; 604/317
[58] Field of Search ............... 128/745, 760, 897, 898; 604/294, 317; 33/200, 483, 493, 494, 755, 759

[56] References Cited

U.S. PATENT DOCUMENTS

| | | |
|---|---|---|
| 780,948 | 1/1905 | Hales . |
| 1,870,655 | 8/1932 | Schur . |
| 3,533,548 | 10/1970 | Taterka . |
| 3,987,554 | 10/1976 | Pastore . |
| 4,168,779 | 9/1979 | Yokokoji et al. . |
| 4,269,197 | 5/1981 | Gilbard . |
| 4,418,477 | 12/1983 | Montgomery . |
| 4,700,491 | 10/1987 | Rhea, Jr. . |

FOREIGN PATENT DOCUMENTS

| | | |
|---|---|---|
| 0330092 | 8/1989 | European Pat. Off. . |
| 1418337 | 12/1975 | United Kingdom . |
| 1510384 | 5/1978 | United Kingdom . |

Primary Examiner—William E. Kamm
Assistant Examiner—Scott R. Akers
Attorney, Agent, or Firm—Rosenman & Colin

[57] ABSTRACT

The present invention is a tear production measuring sheet that has a pair of measuring strips adapted to be used for the right and left eyes and is disposed side by side in such a manner that the strips have a common scale. Each of the measuring strips is separated from the measuring sheet by a cut formed in the measuring sheet so as to extend around the measuring strip, except for a connection between the measuring strip and the sheet.

4 Claims, 3 Drawing Sheets

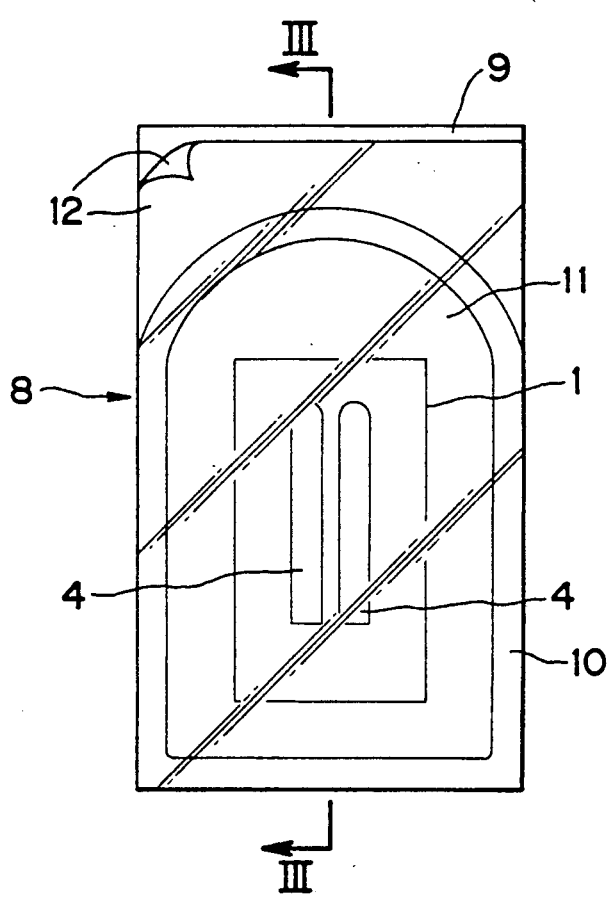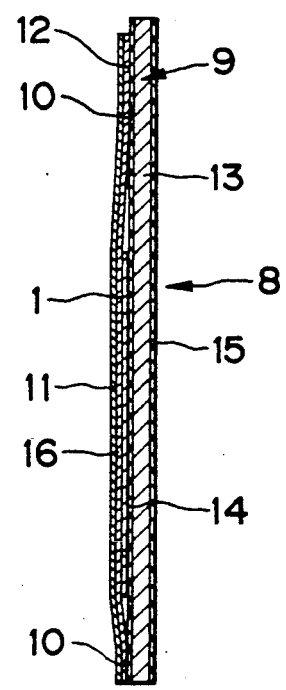

TEAR PRODUCTION MEASURING SHEET AND PACKAGE THEREFOR

BACKGROUND OF THE INVENTION

1. Field of the Invention

The present invention relates to a tear production measuring sheet which is used to measure the tear production of a patient to diagnose a disease or any other abnormality of the eye on the basis of the volume of tear secretion within a unit time.

2. Prior Art

Among measuring strips used for the above-described purpose, Shirmer test strips have hitherto been known. These strips are made of filter paper, and they each have a width of about 5 mm and a length of about 42 mm. Each strip has a semi-circular tip, and a triangular notch formed on one side of the strip at a location of about 5 mm from the tip. In use, the semi-circular tip portion is bent at the notch, and it is then placed inside the lower eye-lid of a patient. Tear secretion infiltrates into the measuring strip and transmits therein. The amount of tear secretion is determined by visually observing the extent to which the filter paper forming the strip is wetted within a unit time.

For instance, if the unit time is five minutes, a length of the moistened area ranging from 10 to 30 mm (usually 15 mm or thereabouts) is regarded as a normal value. The range of normal values lowers with an increase in the age of patients, and, when the patient is above sixty, the amount of secretion can be considerably small. Lengths below 5 mm are, however, regarded as abnormal values.

PROBLEMS TO BE SOLVED BY THE INVENTION

The conventional measuring strips are not scaled. Accordingly, the extent to which they are wetted with tears has to be visually measured, as stated above. If it is necessary to accurately measure the extent of wetting, a separate scale has to be applied. Thus, measurement has to be performed with low levels of efficiency and hygienic standards. In order to eliminate these drawbacks, the applicant of the present invention has previously proposed scaled measuring strips. Another drawback of the conventional measuring strips is that they are identical in construction, without any distinctive correspondence to the left and right eyes. As a result, there is a risk that, during a measuring operation, the strips individually used for the left and right eyes may become indistinguishable from each other, thereby making it necessary to re-start the measuring operation. This problem could be overcome if left and right paired measuring strips have marks provided thereon in some form or other to indicate which of the strips is for the right eye and which is for the left. However, special provision of such marks should be avoided from the viewpoint of production cost. On the other hand, if the strips have to be marked each time a measuring operation is performed, this is troublesome and inefficient.

SUMMARY OF THE INVENTION

Accordingly, an object of the present invention is to provide a tear production measuring sheet having measuring strips as left and right paired measuring strips that can be distinguished from each other in correspondence with their individual use of the right and left eyes.

Another object of the present invention is to provide a package for such a tear production measuring sheet that sealingly contain therein the measuring sheet and that can be easily opened when the measuring sheet is to be used.

MEANS TO SOLVE THE PROBLEMS

There is provided according to the present invention a tear production measuring sheet comprising a measuring sheet member made of a water-absorbing base material and having on the surface thereof, a scale printed on the surface of the sheet at its longitudinal center and a set of numbers printed on the sheet surface on either side of the scale, and a pair of measuring strips adapted to be used for the right and left eyes and disposed side by side in such a manner that each of the measuring strips has on the surface thereof a part of the scale and one set of the numbers, each of the measuring strips being separated from the remaining part of the measuring sheet by a cut formed in the measuring sheet in such a manner as to extend around the measuring strip, except for a connection between the measuring strip and the remaining part.

The measuring strip on the right side has a first scale part extending along the left edge thereof and a first number set arranged on the right side of the first scale part, while the measuring strip on the left side has a second scale part extending along the right edge thereof and a second number set arranged on the left side of the second scale part, so that it is possible to distinguish one of the measuring strips to be used for the right eye and the other to be used for the left eye from each other by the position of the scale part and the number set in each of the strips.

Each of the measuring strips is provided with a bending means for bending a tip portion of the measuring strip which is adapted to be placed inside the lower eye-lid. The bending means preferably comprises one line selected from the group consisting of a perforation, a score line, and a printed indication line.

According to another aspect of the present invention, there is provided a package for a tear production measuring sheet comprising a thin mount, and a transparent cover film heat-sealed to the mount for sealedly covering a tear production measuring sheet disposed on the mount, the cover film also having a portion above the heat-sealed portion which extends downward from the upper end of the cover film in such a manner as to provide a non-heat-sealed portion that facilitates holding the cover film when the package is to be opened.

BRIEF DESCRIPTION OF THE DRAWINGS

The present invention will be more clearly understood from the following description made with reference to the accompanying drawings, in which

FIG. 2 is a front view of a package in which the measuring sheet shown in FIG. 1 is sealed;

FIG. 3 is a longitudinal sectional view taken along the line III—III shown in FIG. 2.

PREFERRED EMBODIMENTS OF THE INVENTION

Figure 1:
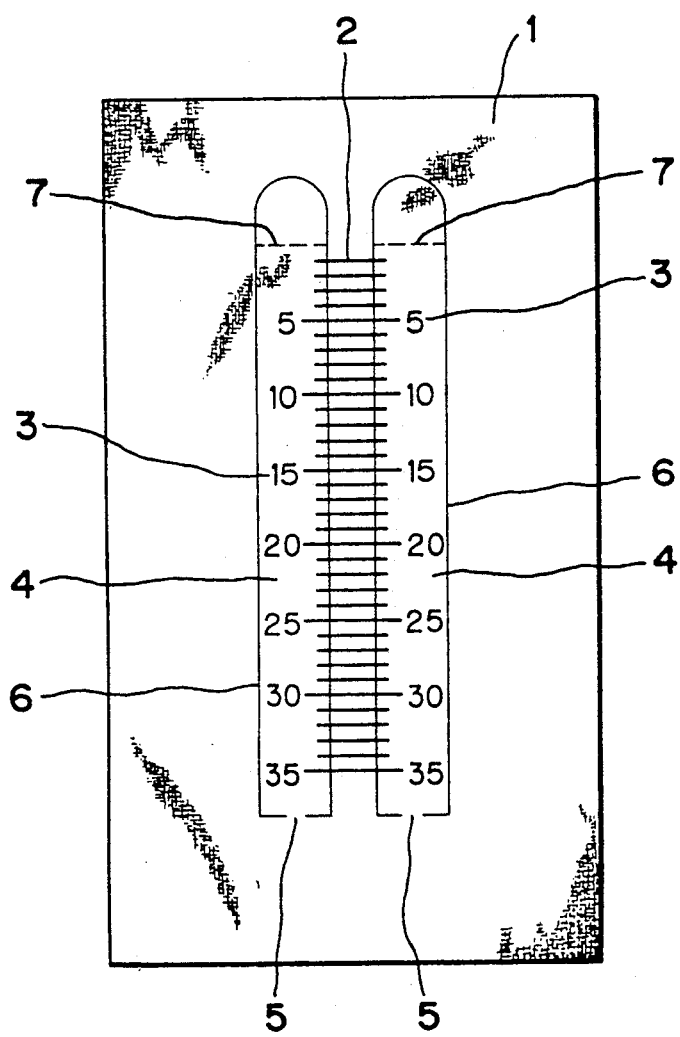
FIG. 1 is a front view of a tear production measuring sheet according to the present invention.

The present invention will now be described with reference to the accompanying drawings. A tear production measuring sheet 1 according to the present invention has, as shown in detail in FIG. 1, a substantially rectangular configuration which is elongated in the up-down direction, as viewed in the drawing, and it is made of a water-absorbing base material which may be filter paper. An example which may be used as the filter paper is Quantitative Filter Paper grade 41 (product of Whatman). The base material of the measuring sheet 1 may not necessarily be filter paper so far as the base material is water-absorbing. For instance, nonwoven fabric may be used. A scale 2 printed on the measuring sheet 1 at its longitudinal center, and a set of numbers 3 are also printed on the sheet surface on either side of the scale. A pair of measuring strips 4 are disposed side by side in such a manner that each of the strips has, on the surface thereof, a part of the scale 2 and one set of numbers 3. In the above-described construction, the measuring strip on the right side has its part of the scale 2 positioned along the left edge thereof and its set of numbers 3 positioned on the right side of this scale part, while the measuring strip on the left side has its part of the scale 2 positioned along the right edge thereof and its set of numbers 3 positioned on the left side of this scale part, so that it is possible to distinguish the measuring strip to be used for the right eye and the other to be used for the left eye from each other by the locations of the scale part and the number set printed on each of the measuring strips. Any printing method employing a typographic printing, gravure printing, or silk-screen printing system can be adopted to print the scale 2 and the numbers 3. However, the adoption of an offset printing system is not preferable from the viewpoint of safety because there is the risk that, during use of the strips, impurities mixed with water adhered to the filter paper may become dissolved in tears and may thus be led into the eyes. The measuring strips 4 are separated from the remaining part of the measuring sheet by cuts (slits) 6 formed in the measuring sheet 1 in such a manner as to extend around the individual measuring strips, except for connections 5 which are positioned at the lower ends of the measuring strips. Needless to say, each connection 5 may be at any other position so far as it is not within the tip portion of the measuring strip. In addition, it is not necessary that one connection be provided for each measuring strip, and a plurality of connections may be provided. Normally, therefore, by virtue of the provision of the connections 5, the measuring strips 4 are prevented from being inadvertently separated from the measuring sheet 1, and they are held to the measuring sheet 1 while positioned on the same plane as the measuring sheet 1. Provided on each measuring strip 4 is a perforation 7 for bending the tip portion which is adapted to be placed inside the lower eye-lid. The perforation may be substituted by a score line formed on each measuring strip. Alternatively, a simple indication may be provided on each measuring strip by printing. Since the tip portions of the measuring strips 4 will be brought into contact with the lower eye-lids, they should preferably be semi-circular so that they do not hurt the eyes.

In use, after the measuring strip 4 on the right side, for instance, is lifted from the measuring sheet 1 by utilizing the cut 6, the measuring strip is held, and it is pulled away from the measuring sheet 1 to be broken off from the connection 5. The measuring strip 4 on the left side is similarly broken off from the measuring sheet. Subsequently, the tip portions of the measuring strips are bent by utilizing the perforation 7, thereby being ready for use. Since there is difference, between the measuring strip on the right side and that on the left side, in the position of the scale part printed on the surface of each measuring strip 4 as well as the position of the number set relative to the associated scale part, if this difference is only recognized, it is possible to use the pair of measuring strips while they are distinguished from each other in correspondence with their individual use for the right and left eyes.

Next, a package according to the present invention will be described in detail with reference to FIGS. 2 and 3.

A package 8 comprises, as will be understood from FIG. 2, a thin mount 9 having a substantially rectangular configuration which is elongated in the up-down direction, as viewed in the figure, and a transparent cover film 11 having, at a peripheral portion thereof, a heat-sealed portion 10 bonded to the mount 9 for sealedly covering a tear production measuring sheet 1, such as that described above, disposed on the mount. A portion of the cover film above the heat-sealed portion 10 preferably extends downward from the upper end thereof in such a manner as to provide a non-heat-sealed portion 12 that facilitates holding the cover film 11 when the package 8 is to be opened.

As will be apparent from FIG. 3, the mount 9 comprises a base material 13 such as paper, a heat-sealing resin layer 14 coated on a front surface of the base material, and an overcoat (of, e.g., nitrocellulose) 15 for protecting a printed surface on the rear surface of the base material 13. If the base material 13 is sterilized with an ethylene oxide gas, as will be described later, it must possess adequate permeability, and it is preferable to use, for example, sterilizing paper. In this case, the mount 9 should preferably possess an air resistance of not more than 5000 sec/100 cc. With respect to materials for the heat-sealing resin layer, although the use of ethylene-vinyl acetate copolymer is preferable, it is possible to use vinyl acetate, vinyl chloride-vinyl acetate copolymer, or the like. With respect to the cover film 11, although glassine paper might be used, polyethylene terephthalate is used in order to assure good transparency, with a heat-sealing resin layer 16 of polypropylene or polyethylene being coated on the reverse surface to enable heat sealing. When the mount 9 and the cover film 11 are processed by a heat sealer while their heat-sealing resin layers 14 and 16 face each other, the resin layers are fusion-bonded together, thereby advantageously allowing these members to be integrally joined together.

Figure 4:
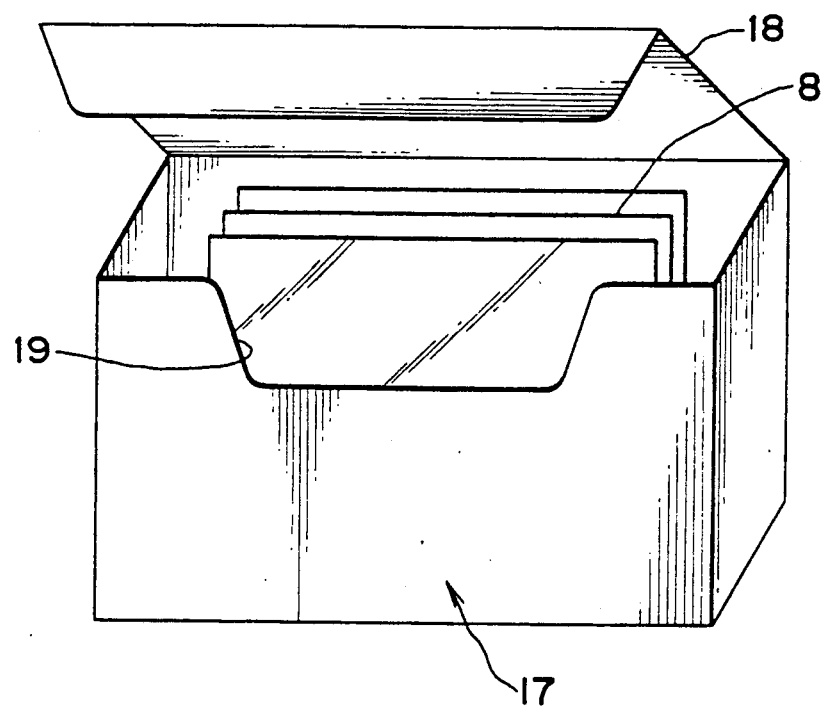
FIG. 4 is a perspective view of a decorated box, showing a state in which packages according to the present invention are packed.

Packages 8, each being such as that described above, are sterilized with an ethylene oxide gas, either one by one or after they are packed, in another process, in a decorated box 17, shown in FIG. 4. A different sterilizing method such as heating sterilization or radiation sterilization may, of course, be adopted.

The decorated box 17 has a configuration which is horizontally elongated, and has an upper cover 18 which can open upward. One of the horizontally elongated sides has a notch portion 19 formed along the upper edge thereof. A predetermined number of packages 8 are packed in the decorated box while they are laid horizontally and are standing on their longitudinal edges. Accordingly, the notch portion 19 enables the packages 8 in this posture to be easily taken out from the upper portion of the decorated box 17. When one of the packages 8 has thus been taken out, if, as described before, the upper portion of the cover film 11 is held and pulled away from the mount 9, the cover film 11 peels off from the heat-sealed portion 10 to become separated, thereby rendering the package open. When the package is thus opened, the measuring sheet 1 is taken out, and it is then used to perform the operation of measuring a tear secretion amount in the manner described before.

EFFECT OF THE INVENTION

As described above, a tear secretion mount measuring sheet according to the present invention, which has a pair of measuring strips individually usable for the right and left eyes, is sealed in one package. The sheet is therefore very convenient for use and efficient for a measuring operation. Each measuring strip has its greater part separated from the sole measuring sheet by a slit, but it is linked to the measuring sheet by at least one joint. Accordingly, each measuring strip is prevented from being separated from the measuring sheet and is held in place until its use. When it is to be used, however, the measuring strip can be broken off from the measuring sheet very quickly, simply, and easily. Since there is difference, between the measuring strip on the right side and that on the left side, in the position of the scale part printed on the surface of each measuring strip as well as the position of the number set relative to the associated scale part, if this difference is only recognized, the pair of measuring strips can be used while being distinguished from each other in correspondence with their individual use for the right and left eyes, and there is no need to provide any special means of discrimination.

What is claimed is:

1. A tear production measuring sheet comprising a measuring sheet made of a water-absorbing base material, said measuring sheet having on the surface thereof a scale printed on the surface of the sheet at its longitudinal center and a set of numbers printed on the sheet surface on either side of said scale, and a pair of measuring strips for the right and left eyes disposed side by side in such a manner that each of said measuring strips has on the surface thereof a part of said scale and one set of said numbers, a cut formed in said measuring sheet in such a manner as to extend around each of the measuring strips with a connection between the measuring strip and the remaining part of said measuring sheet positioned at the bottom end of the measuring strip.

2. A tear production measuring sheet according to claim 1, wherein the measuring strip on the right side has a first scale part extending along the left edge thereof and a first number of set arranged on the right side of said first scale part while the measuring strip on the left side has a second scale part extending along the right edge thereof and a second number set arranged on the left side of said second scale part so that it is possible to distinguish one of said measuring strips to be used for the right eye and the other to be used for the left eye from each other by the position of the scale part and the number set in each of said strips.

3. A tear production measuring sheet according to claim 1, wherein each of said measuring strips has a tip portion and bending means for bending said tip portion, said bent tip portion being adapted to be placed inside the lower eye-lid.

4. A tear production measuring sheet according to claim 3, wherein said bending means comprises one line selected from the group consisting of a perforation, a score line, and a printed indication line.

* * * * *